United States Patent
Begley et al.

(10) Patent No.: US 10,817,920 B2
(45) Date of Patent: Oct. 27, 2020

(54) SYSTEM AND METHOD FOR MANAGING SELECTION OF PRESCRIPTION DRUG PLANS

(71) Applicant: Truveris, Inc., New York, NY (US)

(72) Inventors: Kristin Begley, New York, NY (US); Leon Greene, Jersey City, NJ (US); Anthony J. Loiacono, Bayonne, NJ (US); Tom Staloch, Prior Lake, MN (US)

(73) Assignee: Truveris, Inc., New York, NY (US)

( * ) Notice: Subject to any disclaimer, the term of this patent is extended or adjusted under 35 U.S.C. 154(b) by 746 days.

(21) Appl. No.: 13/999,121

(22) Filed: Jan. 16, 2014

(65) Prior Publication Data

US 2014/0201021 A1  Jul. 17, 2014

Related U.S. Application Data

(60) Provisional application No. 61/753,530, filed on Jan. 17, 2013.

(51) Int. Cl.
| | |
|---|---|
| *G06Q 30/06* | (2012.01) |
| *G16H 40/20* | (2018.01) |
| *G16H 50/70* | (2018.01) |
| *G16H 20/00* | (2018.01) |
| *G06Q 50/22* | (2018.01) |

(52) U.S. Cl.
CPC ......... *G06Q 30/0611* (2013.01); *G06Q 50/22* (2013.01); *G16H 20/00* (2018.01); *G16H 40/20* (2018.01); *G16H 50/70* (2018.01)

(58) Field of Classification Search
CPC .... G06Q 30/0611; G06Q 50/22; G06Q 10/10; G06Q 40/08

USPC .................................................. 705/2–3
See application file for complete search history.

(56) References Cited

U.S. PATENT DOCUMENTS

| | | | |
|---|---|---|---|
| 5,307,262 A | 4/1994 | Ertel | |
| 8,185,415 B2 * | 5/2012 | Rosen | G06Q 10/10 705/35 |
| 2001/0037216 A1 | 11/2001 | Oscar et al. | |
| 2002/0029158 A1 * | 3/2002 | Wolff | G06Q 30/06 705/4 |
| 2002/0103680 A1 | 8/2002 | Newman | |
| 2002/0111832 A1 | 8/2002 | Judge | |
| 2005/0273360 A1 | 12/2005 | Drucker et al. | |
| 2006/0089862 A1 | 4/2006 | Anandarao et al. | |
| 2007/0233516 A1 | 10/2007 | Howe et al. | |
| 2010/0145724 A1 * | 6/2010 | Kalies, Jr. | G06Q 50/22 705/2 |
| 2013/0218749 A1 * | 8/2013 | Mani | G06Q 40/04 705/37 |

(Continued)

OTHER PUBLICATIONS

Ha Huskamp et al. "The Medicare prescription drug benefit: how will the game be played" Health Affairs 19, No. 2 (2000) 8-23.*

Google Patents Search, Mar. 22, 2018, 6 pages.

*Primary Examiner* — Eliza A Lam (74) *Attorney, Agent, or Firm* — Sheppard, Mullin, Richter & Hampton LLP (57) ABSTRACT

A system and method for managing selection of a prescription drug plan, based on generating a request for proposal (RFP), submitting the RFP to prescription benefit management (PBM) vendors, receiving bids from PBM vendors, and calculating weighted scores of the bids to determine total score for the plan.

15 Claims, 8 Drawing Sheets

(56) References Cited

U.S. PATENT DOCUMENTS

2014/0039911 A1 2/2014 Iyer
2014/0201021 A1 7/2014 Begley et al.

* cited by examiner

SYSTEM AND METHOD FOR MANAGING SELECTION OF PRESCRIPTION DRUG PLANS

CROSS REFERENCE TO RELATED APPLICATION

This application claim the benefit under 35 U.S.C. 119(e) of U.S. Patent Application No. 61/753,530, filed Jan. 17, 2013, which is hereby incorporated by reference herein in its entirety.

FIELD OF THE INVENTION

Embodiments of the invention relate generally to prescription drug plans and, more specifically, to electronic management of a request for proposal (RFP) and corresponding bids for selecting a prescription drug plan.

BACKGROUND OF THE INVENTION

Presently, sponsors of pharmacy benefit management plans typically enter into a request for proposal ("RFP") process every few years in order to maintain market competitive benefits, which may be valued at $5 Million to $500 Million in plan spend per year. This process entails a solicitation of competitive bids from Pharmacy Benefit Manager ("PBM") vendors serving the marketplace and an evaluation of the submitted proposals. A problem that arises with current implementations of RFPs is that plan sponsors (business entities, corporations, etc. with health- and medical-insurable employees) are reliant upon the cost projections provided by the PBM vendors, which often do not fairly or accurately represent the value of the bids being presented.

Due to the complexities associated with the pharmacy benefit industry and pricing methodologies for prescription drugs, evaluation of PBM bids are typically subject to the calculations or stated cost projections provided by the vendors themselves. Pricing calculations are reliant upon specialized industry knowledge, highly technical algorithmic pricing calculations, subjective cost projection methodologies, powerful computer processing equipment, and subscription to third party data services for clinical and pricing classification data required to calculate pharmacy claims cost according to bid terms. Absent the aforementioned elements, calculating the costs of any one RFP bid, much less a multitude of bids typically submitted by various PBM vendors in the course of an RFP process, can not be done in a reasonable period of time to provide maximum savings to clients and patients.

Furthermore, due to the interpretive nature of contract language, PBM bid contract terms may be manipulated through subtlety in language and nuance in terminology, which cannot be fairly assessed to compare vendor RFP submissions. As a result, RFP submissions are highly subjective and prone to manipulation by PBM vendors and bids cannot be fairly or objectively assessed by even the most knowledgeable industry professionals and data analysts due to the unmanageably large claims data sets, complex calculations involving determinations of drug classification and application of pricing terms, reliance upon costly subscription services for third party data elements, and variety of terms and pricing proposals provided in the limited period of time allowed to complete an RFP process.

By so structuring the bids, PBMs thrive upon a bid process in which the plan sponsors are unable to assess the relative value of the proposed contracts in objective terms and are reliant upon the bidder's own projections. As such, a solution is required to provide an improved method for conducting PBM request for proposals and calculating the projected costs of the plan subject to RFP bid terms and pricing proposals, resulting in an unbiased assessment of deal terms and pricing projections, presented on a consistent basis across RFP submissions.

BRIEF DESCRIPTION OF THE DRAWINGS

The present invention is illustrated by way of example, and not by way of limitation, and will become apparent upon consideration of the following detailed description, taken in conjunction with the accompanying drawings, in which like reference characters refer to like parts throughout, and in which.

SUMMARY OF THE INVENTION

The present invention relates to a computer-implemented system and method for managing a request for proposal (RFP), said method characterized by:

generating, using a programmed computer, said RFP for a client entity;

distributing, using said programmed computer, said RFP to a plurality of respondent entities selected to participate in submission of a bid for said RFP;

receiving an electronic confirmation from one or more of said plurality of respondent entities acknowledging participation in submitting said bid for said RFP;

receiving, using said programmed computer, bids from said plurality of respondent entities having acknowledged participation;

adjudicating, using said programmed computer, each of said bids received to provide a standardized comparison between said bids;

projecting, using said programmed computer, costs forward by applying inflation parameters across each of said bids for claim sets associated with said RFP;

scoring, using said programmed computer, each of said bids; and presenting, using said programmed computer, one or more prevailing bids to said client entity.

DETAILED DESCRIPTION

Embodiments of the invention provide methods for managing selection of prescription drug plans.

In the following description, numerous details are set forth. It will be apparent, however, to one skilled in the art, that the present invention may be practiced without these specific details. In some instances, well-known structures and devices are shown in block diagram form, rather than in detail, in order to avoid obscuring the present invention.

Some portions of the detailed descriptions are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, as apparent from the above discussion, it is appreciated that throughout the description, discussions utilizing terms such as "initiating", "receiving", "determining", "generating", "constructing", "transmitting", "adjudicating", "scoring", "calculating", "processing", "presenting" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The present invention also relates to an apparatus for performing the operations herein. This apparatus may be specially constructed for the required purposes or it may comprise a general purpose computer selectively activated or reconfigured by a computer program stored in the computer. Such a computer program may be stored in a computer readable storage medium, such as, but not limited to, any type of disk including floppy disks, optical disks, CD-ROMs and magnetic-optical disks, read-only memories (ROMs), random access memories (RAMs), EPROMs, EEPROMs, magnetic or optical cards, flash memory devices including universal serial bus (USB) storage devices (e.g., USB key devices) or any type of media suitable for storing electronic instructions, each of which may be coupled to a computer system bus.

The algorithms and displays presented herein are not inherently related to any particular computer or other apparatus. Various general purpose systems may be used with programs in accordance with the teachings herein or it may prove convenient to construct more specialized apparatus to perform the required method steps. The required structure for a variety of these systems will be apparent from the description above. In addition, the present invention is not described with reference to any particular programming language. It will be appreciated that a variety of programming languages may be used to implement the teachings of the invention as described herein.

The present invention may be provided as a computer program product, or software, that may include a machine-readable medium having stored thereon instructions, which may be used to program a computer system (or other electronic devices) to perform a process according to the present invention. A machine-readable medium includes any mechanism for storing or transmitting information in a form readable by a machine (e.g., a computer). For example, a machine-readable (e.g., computer-readable) medium includes a machine (e.g., a computer) readable storage medium (e.g., read only memory ("ROM"), random access memory ("RAM"), magnetic disk storage media, optical storage media, flash memory devices, etc.), a machine (e.g., computer) readable transmission medium (non-propagating electrical, optical, or acoustical signals), etc.

Figure 1:
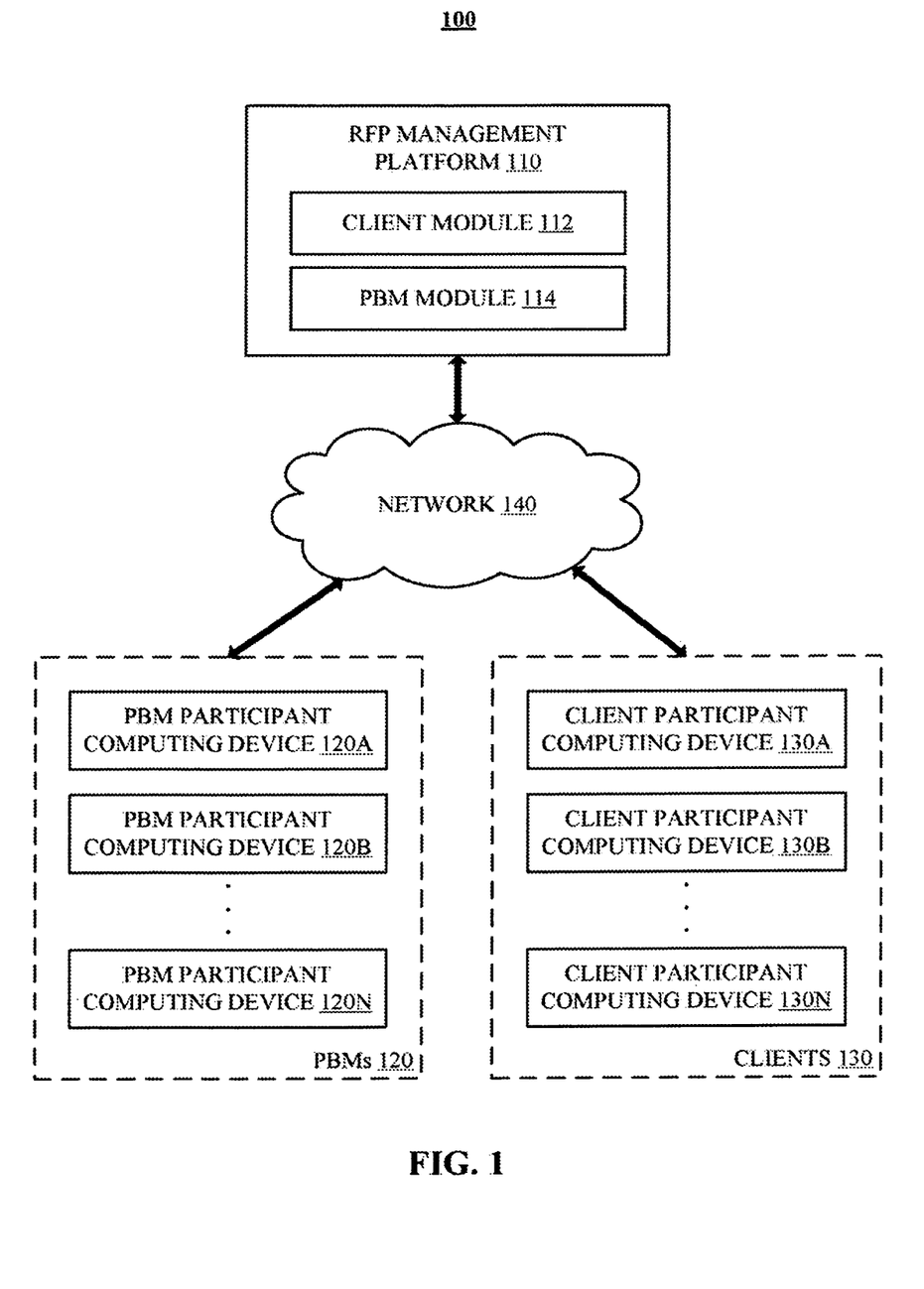
FIG. 1 is a block diagram illustrating an exemplary computer network in which embodiments of the present invention may operate.

FIG. 1 is a block diagram illustrating an exemplary computer network 100 in which embodiments of the present invention may operate. Referring to FIG. 1, computer network 100 may be comprised of at least one RFP management platform 110, a plurality of computing devices 120A-120N associated with PBMs 120 and a plurality of computing devices 130A-130N associated with clients 130 (or one or more representative entities authorized to act on behalf of a client). Computing devices associated with PBMs 120 and clients 130 may be communicatively coupled, via a network 140, to one or more processing and storage accessible components of RFP management platform 110. Network 140 may be a private network (e.g., a local area network (LAN), wide area network (WAN), intranet, etc.) or a public network (e.g., the Internet).

RFP management platform 110 may be enabled by one or more computing modules configured to process various processes of the present invention, as described herein. For example, RFP management platform 110 may be comprised of a client module 112 and a PBM module 114. In one embodiment, client module 112 may be configured to manage all aspects of a client's interaction with RFP management platform 110, while PBM module 114 may be configured to manage all aspects of a PBM's interaction with RFP management platform 110. In another embodiment, client module 112 may be primarily configured to manage all aspects of generating a RFP for bidding by participating PBMs, while PBM module 114 may be configured to manage all aspects of adjudicating and scoring bids received from participating PBMs in response to the RFP.

Figure 2:
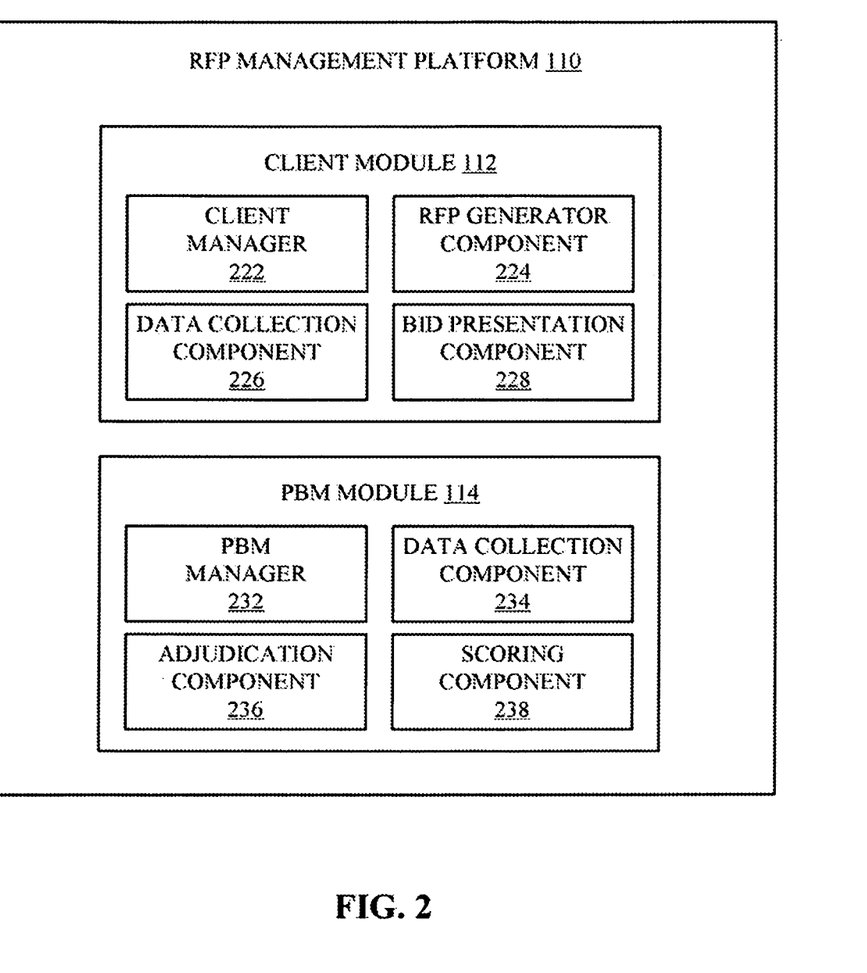
FIG. 2 is a block diagram illustrating exemplary components enabling an RFP management platform, as illustrated in the exemplary computer network of FIG. 1.

Client module 112 may be comprised of a plurality of components for processing instructions to execute methods associated with conducting an RFP process involving interactions by, or gathering of data relating to, clients 130. Referring to FIG. 2, client module 112 may comprise, for example, a client manager 222, a RFP generator component 224, a data collection component 226 and a bid presentation component 228. Client manager 222 may be configured to control all aspects of managing client side interactions with RFP management platform 110 including, but not limited to, enabling and controlling components 224, 226 and 228. Component 224, 226 and 228 may be configured, for example, to generate an RFP, determine whether criteria required for participating in the RFP are satisfied, identify and communicate RFP parameters to select PBMs 120, retrieve existing plan data related to clients 130, present bid information to assist in a bid selection process and any other applicable processes or corresponding determinations for administering a RFP on behalf of a participating client entity.

PBM module 114 may be comprised of a plurality of components processing instructions to execute methods associated with conducting an RFP process involving interactions by, or gathering of data relating to, PBMs 120. Referring to FIG. 2, PBM module 114 may comprise, for example, a PBM manager 232, a data collection component 234, an adjudication component 236 and a scoring component 238. PBM manager 232 may be configured to control all aspects of managing PBM side interactions with RFP management platform 110 including, but not limited to, enabling and controlling components 234, 236 and 238. Component 234, 236 and 238 may be configured, for example, to manage distribution of an RFP and related client data to participating PBMs, enable bid preparation and submission by a PBM, adjudicate proposed bids, score bids submitted by a PBM and any other applicable processes or corresponding determinations for administering submission of a bid on behalf of a participating PBM.

Those skilled in the art will appreciate that RFP management platform 110 may be configured with more or less modules and components to conduct the methods described herein with reference to FIGS. 3-7. As illustrated in FIGS. 3-7, each of corresponding methods 300, 400, 500, 600 and 700 may be performed by processing logic that may comprise hardware (e.g., circuitry, dedicated logic, programmable logic, microcode, etc.), software (such as instructions run on a processing device), or a combination thereof. In one embodiment, methods 300, 400, 500, 600 and 700 may be performed by one or more processing components associated with modules 112 and 114 of RFP management platform 110.

Figure 3:
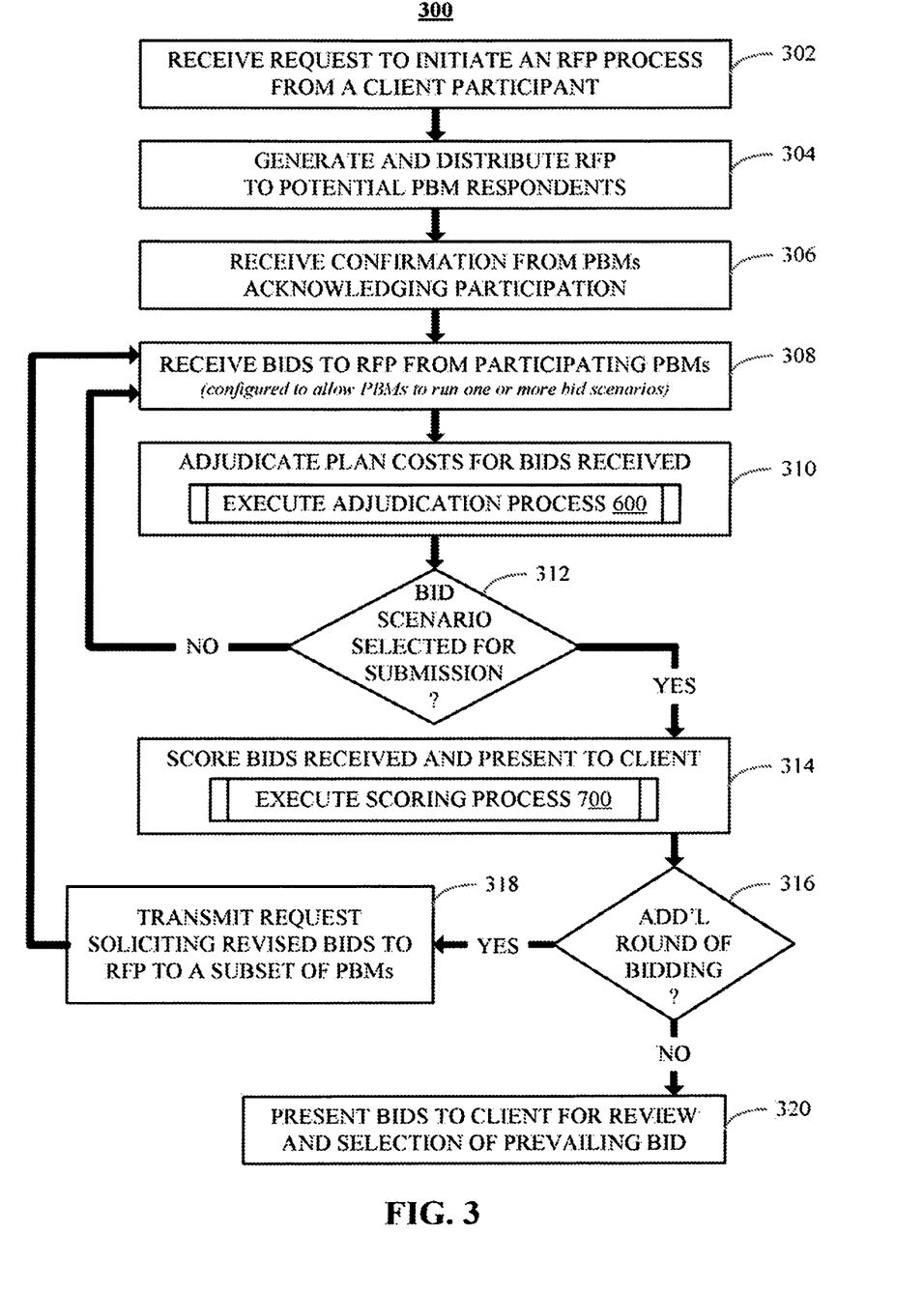
FIG. 3 is a flow diagram illustrating an embodiment of a method for managing a request for proposal (RFP) between a client entity and prescription benefit managers (PBMs).

FIG. 3 is a flow diagram illustrating a method 300 for managing an RFP between a client and participating PBMs, according to an embodiment of the invention. Referring to FIG. 3, method 300 may be initiated upon receiving, at block 302, a request to initiate an RFP process. For example, method 300 may be initiated when a client participant requests a new RFP. Upon receiving the request, the new RFP may be generated and distributed, at block 304, to potential PBM respondents. Confirmation (e.g. electronic, oral, etc.) may be received, at block 306, from PBM participants acknowledging receipt and participation in the RFP evaluation.

Bid scenarios may be received, at block 308, from participating PBMs in response to the RFP. RFP management platform 110 may be configured to permit participating PBMs to execute a plurality of bid scenarios (i.e., present varying costs, terms and definitions) and allow for each of the bid scenarios to be adjudicated, at block 310, prior to submitting a bid by PBMs in response to the RFP. When method 300 determines, at block 312, that a bid scenario has been selected to be submitted as the bid in response to the RFP, each of the bids received from participating PBMs may be scored, at block 314, for presentation to the client. However, if the bid scenario is not selected at block 312, due to missing information or error, the bid may be returned to the participating PBM at block 308.

In one embodiment, if a determination is made, at block 316, that additional rounds of bidding will be engaged, due to determination of an inadequate scores for the bids received, then method 300 may be configured to transmit, at block 318, a request soliciting revised bids to the RFP to a subset of the participating PBMs. The subset may be determined, for example, based on scores associated with the original bids submitted by the participating PBMs. Once a determination is made, at block 316, that no additional rounds of bidding will be engaged, final bids from the subset of participating PBMs may be presented, at block 320, to the client for review and selection of a prevailing bid. "Prevailing bids" may be defined as bids characterized by scores illustrative of significantly favorable projected-cost structures, market competitive benefits, enhanced cost savings over a projected period of time, etc.

Figure 4:
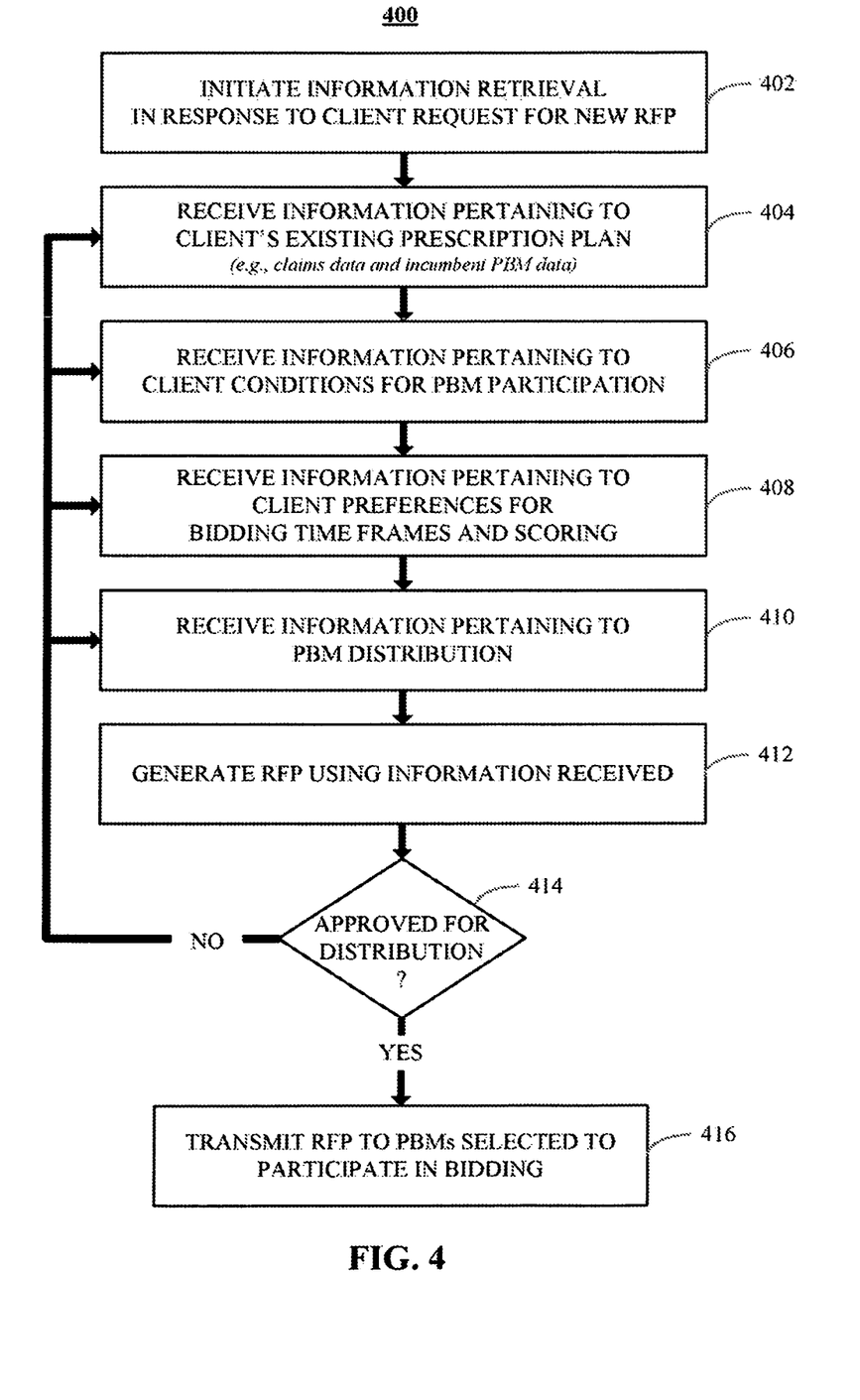
FIG. 4 is a flow diagram illustrating an embodiment of a method for generating an RFP.

FIG. 4 is a flow diagram illustrating a method 400 for generating a RFP, according to an embodiment of the invention. Referring to FIG. 4, method 400 may be initiated upon receiving an indication from RFP management platform 110 that a new RFP is to be generated for a client. Information retrieval for generating the new RFP may be initiated, at block 402, in response to the client request for the RFP. Method 400 may receive a variety of information, at blocks 404-410, pertaining to client's existing prescription drug plan (e.g., prescription-claims data, formulary data and incumbent PBM data, etc.), client conditions for PBM participation, client preferences for bidding time frames and scoring of bids received, distribution of the RFP to select PBMs and any other information relevant to generating the RFP and enabling bidding thereon. Once the RFP has been generated, at block 412, and approved for distribution, at block 414, the RFP may be transmitted, at block 416, to PBMs selected to receive an invitation to participate in the RFP bidding process. If the RFP is not approved for distribution, at block 414, due to a lack of information or error in the information, additional information may be retrieved from client and provided to blocks 404-410 to regenerate the RFP.

Figure 5:
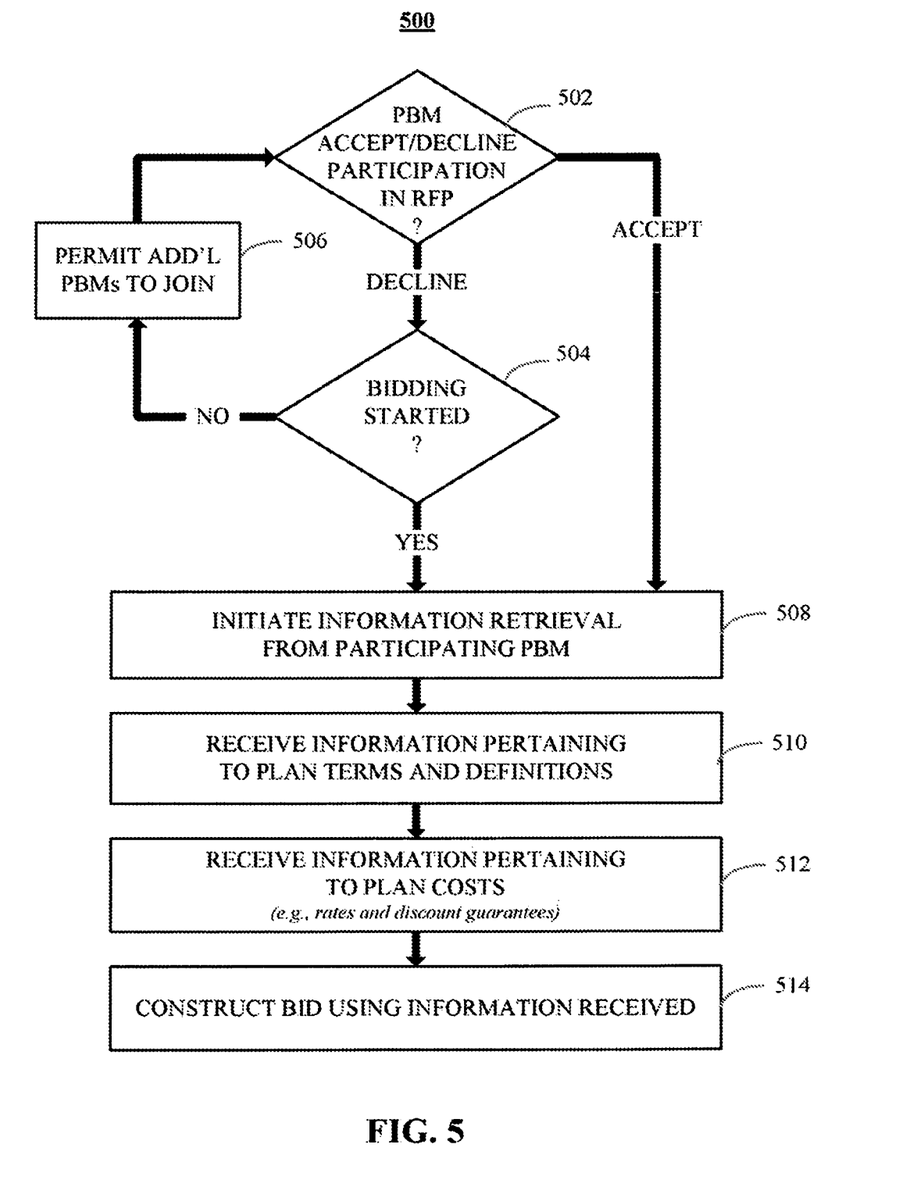
FIG. 5 is a flow diagram illustrating an embodiment of a method for constructing a bid in response to an RFP.

FIG. 5 is a flow diagram illustrating a method 500 for constructing a bid in response to an RFP, according to an embodiment of the invention. Referring to FIG. 5, method 500 may be initiated upon determining, at block 502, that a PBM has accepted an invitation to participate in the RFP bidding process. If the PBM has been accepted the invitation, at block 502, the process continues to block 508. In one embodiment, method 500 may continue to receive acknowledgements from PBMs that wish to participate in the RFP bidding process (even if a PBM initially declines an invitation to participate at block 502) until bidding begins. For example, a time period may be set for receiving acknowledgements to participate before actual bidding is opened to PBMs. Method 500 may determine, at block 504, whether the bidding process has started. If not, additional PBMs may be permitted, at block 506, to acknowledge participation in bidding on the RFP.

Information retrieval for constructing a bid for a participating PBM may be initiated, at block 508, once bidding on the RFP is started. Method 500 may receive various information, at block 510 and block 512, pertaining to plan terms, definitions and costs (e.g. rates and discount guarantees) the participating PBM is offering or agreeing to provide. Once the required information is submitted by a participating PBM, a proposed bid may be constructed, at block 514, to be received and processed at RFP management platform 110. As identified in method 300 illustrated in FIG. 3, an adjudication process may be engaged, at block 310, for bids received from participating PBMs. The adjudication process, which is described in additional detail with reference to method 600 illustrated in FIG. 6, may allow the standardization of bids received across the pool of participating PBMs.

Figure 6:
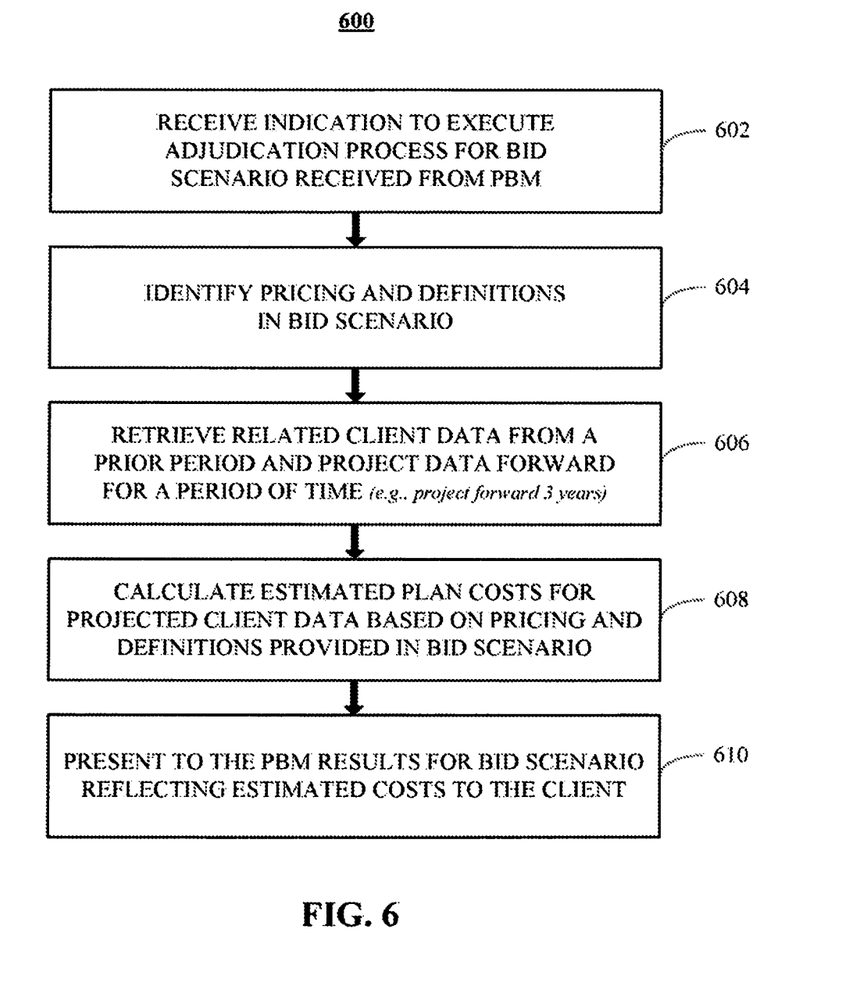
FIG. 6 is a flow diagram illustrating an embodiment of a method for implementing an adjudication process.

FIG. 6 is a flow diagram illustrating a method 600 for implementing an adjudication process, according to an embodiment of the invention. Referring to FIG. 6, method 600 may be initiated upon receiving, at block 602, an indication to execute an adjudication process for a bid scenario. Pricing and definitions associated with a corresponding plan represented by the bid scenario may be identified, at block 604. Additionally, related client data from a prior period (the same data provided to a participating PBM in constructing a bid) is retrieved, at block 606, and projected forward (i.e., inflated) for a specified period of time—e.g., three (3) years. Forward projections may be based upon configurable parameters set separately for each of the three (3) projection years.

For each year of a projection, an inflation percentage may be applied to a claim set based upon division of drug claims into brand, generic, and specialty drug classifications utilizing data indicators provided by third party data sources (e.g., licensed industry databases). Drug classification may be determined on a claim by claim basis using a custom configured algorithm in order to ensure that inflation is applied consistently across all PBM bids, regardless of the PBM drug classification terms selected. For each classification type (brand, generic, and specialty) and each year of the projection, a stored percentage value may be applied, indicating the utilization inflation percentage and price inflation percentage. As a result, drug spend may be uniformly applied across all PBM bids, but specific to the drug mix and claims contained in the RFP claims data.

Thereafter, estimated plan costs for the projected client data may be calculated, at block 608, based on the pricing and definitions provided in the bid scenario and presented, at block 610, to the PBM for review. If the PBM is satisfied with the estimated costs associated with the bid scenario, the bid may be submitted as the PBM's bid to undergo a scoring process.

Figure 7:
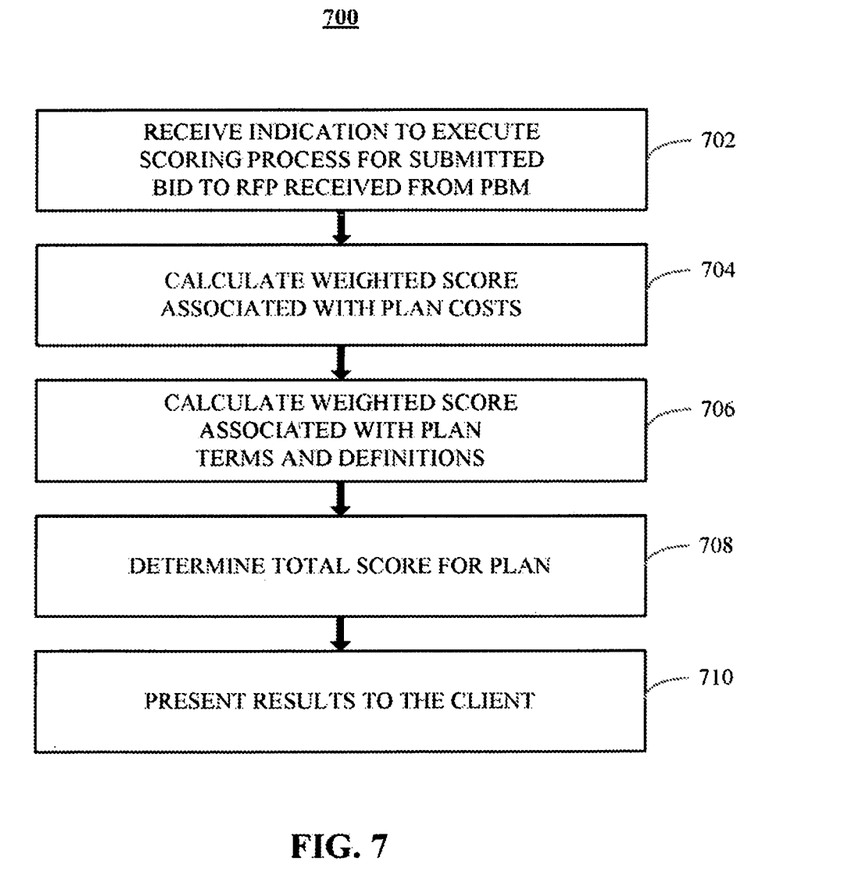
FIG. 7 is a flow diagram illustrating an embodiment of a method for implementing a scoring process.

FIG. 7 is a flow diagram illustrating a method 700 for implementing a scoring process, according to an embodiment of the invention. Referring to FIG. 7, method 700 may be initiated upon receiving, at block 702, an indication to execute a scoring process for a submitted bid to an RFP received from a participating PBM. In implementing the scoring process, method 700 may calculate weighted scores associated with costs of a plan, at block 704. Weighted scores associated with contract terms and definitions of a plan may be calculated at block 706, or weighted scores associated with any other category of a plan submitted in the bid by the participating PBM may be calculated. Scores calculated for one or more categories of the plan may then be used to determine, at block 708, a total score for the plan. The total score for the plan may be presented for consideration to the client originating the RFP at block 710.

In calculating a score for a particular category of the plan, multiple factors underlying the category may be taken into consideration. For example, in calculating a score for the terms and definitions category of the plan, factors relating to agreement and/or disagreement of definitions, PBM services offered, audit and bill review, term and termination of the plan, confidentiality elements, technical definitions of drug pricing classifications, specific pricing discounts, performance guarantees and any other applicable measure may be taken into consideration and assigned a weighted score as a percentage of a total score possible for the category. Scoring percentages and weights may be predefined via administrative settings or be subject to client preferences.

Figure 8:
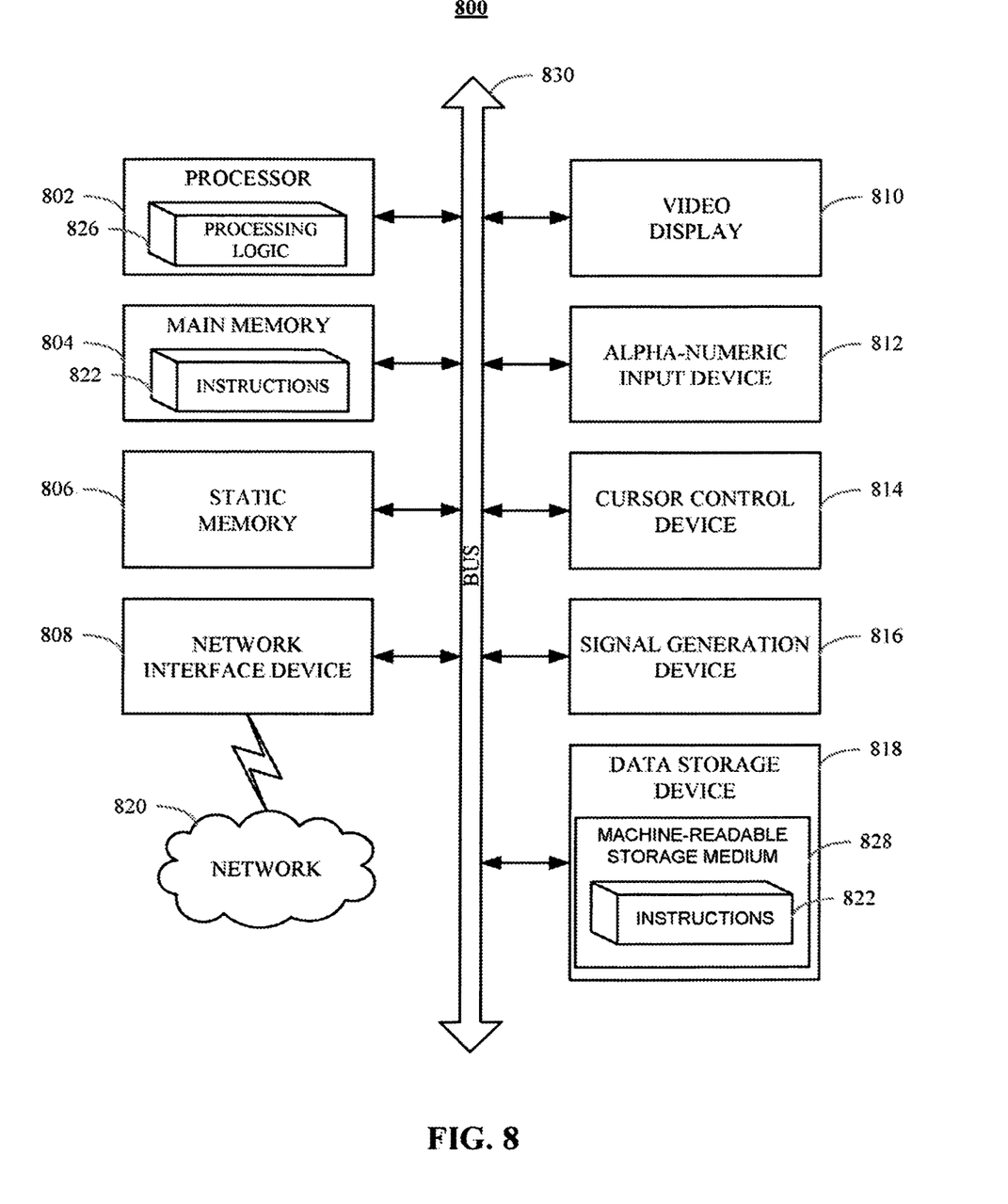
FIG. 8 illustrates a diagrammatic representation of a machine in the exemplary form of a computer system.

FIG. 8 illustrates a diagrammatic representation of a machine in the exemplary form of a computer system 800 within which a set of instructions for causing the machine to perform any one or more of the methodologies discussed herein, may be executed. In alternative embodiments, the machine may be connected (e.g., networked) to other machines in a local area network (LAN), an intranet, an extranet, or the Internet. The machine may operate in the capacity of a server or a client machine in a client-server network environment, or as a peer machine in a peer-to-peer (or distributed) network environment. The machine may be a personal computer (PC), a tablet PC, a set-top box (STB), a personal digital assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The exemplary computer system 800 may be comprised of components, including, a processing device 802, a main memory 804 (e.g., read-only memory (ROM), flash memory, dynamic random access memory (DRAM) (such as synchronous DRAM (SDRAM) or Rambus DRAM (RDRAM), etc.), a static memory 806 (e.g., flash memory, static random access memory (SRAM), etc.), and a data storage device 818, which communicate with each other via a bus 830.

Processing device 802 represents one or more general-purpose processing devices such as a microprocessor, central processing unit, or the like. More particularly, the processing device may be a complex instruction set computing (CISC) microprocessor, reduced instruction set computer (RISC) microprocessor, very long instruction word (VLIW) microprocessor, or processor implementing other instruction sets, or processors implementing a combination of instruction sets. Processing device 802 may also be one or more special-purpose processing devices such as an application specific integrated circuit (ASIC), a field programmable gate array (FPGA), a digital signal processor (DSP), network processor, or the like. Processing device 802 is configured to execute processing logic 826 for performing the operations and steps discussed herein.

Computer system 800 may further include a network interface device 808. Computer system 800 also may include a video display unit 810 (e.g., a liquid crystal display (LCD) or a cathode ray tube (CRT)), an alphanumeric input device 812 (e.g., a keyboard), a cursor control device 814 (e.g., a mouse), and a signal generation device 816 (e.g., a speaker).

Data storage device 818 may include a machine-readable storage medium (or more specifically a computer-readable storage medium) 828 having one or more sets of instructions (e.g., software 822) embodying any one or more of the methodologies of functions described herein. For example, software 822 may store instructions for managing a request for proposal and corresponding bids for selection of a prescription drug plan. Software 822 may also reside, completely or at least partially, within main memory 804 and/or within processing device 802 during execution thereof by computer system 800; main memory 804 and processing device 802 also constituting machine-readable storage media. Software 822 may further be transmitted or received over a network 820 via network interface device 808.

Machine-readable storage medium 828 may also be used to store instructions for managing an RFP and corresponding bids for selection of a prescription drug plan. While machine-readable storage medium 828 is shown in an exemplary embodiment to be a single medium, the term "machine-readable storage medium" should be taken to include a single medium or multiple media (e.g., a centralized or distributed database, and/or associated caches and servers) that store the one or more sets of instructions. The term "machine-readable storage medium" shall also be taken to include any medium that is capable of storing or encoding a set of instruction for execution by the machine that causes the machine to perform any one or more of the methodologies of the present invention. The term "machine-readable storage medium" shall accordingly be taken to include, but not be limited to, solid-state memories, and optical and magnetic media.

Whereas many alterations and modifications of the present invention will no doubt become apparent to a person of ordinary skill in the art after having read the foregoing description, it is to be understood that any particular embodiment shown and described by way of illustration is in no way intended to be considered a limitation of the invention. Therefore, references to details of various embodiments are not intended to limit the scope of the claims, which in themselves recite only those features regarded as the invention.

What is claimed is:

1. A computer-implemented method performed by a computer system for supporting an entity with selection of a prescription drug plan, said method comprising:

receiving a request to initiate a request for proposal (RFP) process from a particular remote client system of a plurality of remote client systems, the request to initiate the RFP process being for a prescription drug plan for a particular entity;

obtaining a particular set of historical drug claims for the particular entity from a remote database;

generating an RFP for the particular entity for the prescription drug plan based on the particular set of historical drug claims obtained from the remote database;

distributing said RFP to a plurality of remote pharmacy benefit manager (PBM) systems to participate in submission of a bid in response to said RFP;

receiving an electronic confirmation from one or more of said plurality of remote PBM systems acknowledging participation in said RFP;

receiving one or more bids containing pricing information and contract terms from the one or more of said plurality of remote PBM systems having acknowledged participation, the pricing information comprising respective pricing terms corresponding to one or more drug claims, the one or more bids each including a corresponding PBM-indicated drug classification for each drug claim of the one or more drug claims;

obtaining, from one or more third party systems, data indicators indicating third-party-indicated drug classifications for the historical drug claims of the particular set of historical drug claims, the third-party-indicated drug classifications including a generic drug classification, a brand drug classification, and a specialty drug classification, the third party systems being different than the remote database, the particular remote client system and the plurality of PBM systems;

classifying each historical drug claim of the particular set of historical drug claims into one or more third-party-indicated drug classifications of the third-party-indicated drug classifications based on the data indicators, the classifying disregarding the corresponding PBM-indicated drug classification;

obtaining, from the one or more third-party systems, price inflation parameters and utilization inflation parameters for each third-party-indicated drug classification of the one or more third-party-indicated drug classifications;

obtaining historical utilization data associated with the particular set of historical drug claims;

using the particular set of historical drug claims from the remote database to project costs forward by applying the price inflation parameters to the pricing information of each bid of said one or more bids based on the one or more third-party-indicated drug classifications, and applying the utilization inflation parameters to the historical utilization data associated with the particular set of historical drug claims;

calculating a corresponding estimated plan cost for each bid of the one or more bids based on the projecting costs forward, the corresponding estimated plan cost of each bid of the one or more bids having accounted for price inflation and utilization inflation based on the same price inflation parameters, the same utilization inflation parameters, and the same third-party-indicated drug classifications;

calculating a contract terms cost for the contract terms of each bid of the one or more bids;

generating scores for each bid of said one or more bids based on the corresponding estimated plan cost and on the contract terms cost; and sending at least one bid of the one or more bids and at least one score of the scores to said particular remote client system to support selection of the drug prescription plan from the one or more bids.

2. The computer-implemented method of claim 1, wherein said plurality of remote PBM systems selected to participate in submission of said bid are identified by said plurality of remote client systems.

3. The computer-implemented method of claim 1, wherein said price inflation parameters are set separately for each year of projection.

4. The computer-implemented method of claim 1, wherein scoring each of said one or more bids comprises at least two scoring elements, wherein a first scoring element is associated with plan costs and a second scoring element is associated with plan terms and definitions.

5. The computer-implemented method of claim 4, wherein said first scoring element and said second scoring element are represented by weighted scoring values.

6. The computer-implemented method of claim 1, further comprising, after the receiving the one or more bids, determining if at least one bid of the one or more bids is approved, and if a particular bid of the at least one bid is not approved, transmitting a request for a revised bid to a subset of said plurality of remote PBM systems.

7. The computer-implemented method of claim 1, further comprising, after the scoring each of said one or more bids, if an inadequate score is determined, transmitting a request for a revised bid to a subset of said plurality of remote PBM systems.

8. The computer-implemented method of claim 6, further comprising re-scoring revised bids received from said subset of said plurality of remote PBM systems.

9. The computer-implemented method of claim 7, further comprising re-scoring revised bids received from said subset of said plurality of remote PBM systems.

10. The computer-implemented method of claim 1, wherein one or more prevailing bids are selected from bids comprising significantly favorable projected-cost structures, market competitive benefits, and enhanced cost savings over a projected period of time.

11. A computer system for supporting an entity with a request for proposal (RFP), comprising:

memory storing program instructions;

one or more processors coupled to said memory, wherein when executing the program instructions the one or more processors is configured to:

receive a request to initiate a request for proposal (RFP) process from a particular remote client system of a plurality of remote client systems, the request to initiate the RFP process being for a prescription drug plan for a particular entity;

obtain a particular set of historical drug claims for the particular entity from a remote database;

generate an RFP for the particular entity for the prescription drug plan based on the particular set of historical drug claims from the remote database;

distribute said RFP to a plurality of remote pharmacy benefit manager (PBM) systems to participate in submission of a bid in response to said RFP;

receive an electronic confirmation from one or more of said plurality of remote PBM systems acknowledging participation in said RFP;

receive one or more bids containing pricing information and contract terms from the one or more of said plurality of remote PBM systems having acknowledged participation, the pricing information comprising respective pricing terms corresponding to one or more drug claims, the one or more bids each including a corresponding PBM-indicated drug classification for each drug claim of the one or more drug claims;

obtain, from one or more third party systems, data indicators indicating third-party-indicated drug classifications for the historical drug claims of the particular set of historical drug claims, the third-party-indicated drug classifications including a generic drug classification, a brand drug classification, and a specialty drug classification, the third party systems being different than the remote database, the particular remote client system and the plurality of PBM systems;

classify each historical drug claim of the particular set of historical drug claims into one or more third-party-indicated drug classifications of the third-party-indicated drug classifications based on the data indicators, the classifying disregarding the corresponding PBM-indicated drug classification;

obtain, from the one or more third-party systems, price inflation parameters and utilization inflation parameters for each third-party-indicated drug classification of the one or more third-party-indicated drug classifications;

obtain historical utilization data associated with the particular set of historical drug claims;

use the particular set of historical drug claims from the remote database to project costs forward by applying the price inflation parameters to the pricing information of each bid of said one or more bids based on the one or more third-party-indicated drug classifications, and applying the utilization inflation parameters to the historical utilization data associated with the particular set of historical drug claims;

calculate a corresponding estimated plan cost for each bid of the one or more bids based on the projecting costs forward, the corresponding estimated plan cost of each bid of the one or more bids having accounted for price inflation and utilization inflation based on the same price inflation parameters, the same utilization inflation parameters, and the same third-party-indicated drug classifications;

calculate a contract terms cost for the contract terms of each bid of the one or more bids;

generate scores for each bid of said one or more bids based on the corresponding estimated plan cost and on the contract terms cost; and send at least one bid of the one or more bids and at least one score of the scores to said particular remote client system to support selection of the drug prescription plan.

12. A non-transitory computer-readable storage medium programmed to include instructions that, when executed by a processing device, cause the processing device to perform a method of managing a request for proposal, said method comprising:

receiving a request to initiate a request for proposal (RFP) process from a particular remote client system of a plurality of remote client systems, the request to initiate the RFP process being for a prescription drug plan for a particular entity;

obtaining a particular set of historical drug claims for the particular entity from a remote database;

generating an RFP for the particular entity for the prescription drug plan based on the particular set of historical drug claims from the remote database;

distributing said RFP to a plurality of remote pharmacy benefit manager (PBM) systems to participate in submission of a bid in response to said RFP;

receiving an electronic confirmation from one or more of said plurality of remote PBM systems acknowledging participation in said RFP;

receiving one or more bids containing pricing information and contract terms from the one or more of said plurality of remote PBM systems having acknowledged participation, the pricing information comprising respective pricing terms corresponding to one or more drug claims, the one or more bids each including a corresponding PBM-indicated drug classification for each drug claim of the one or more drug claims;

obtaining, from one or more third party systems, data indicators indicating third-party-indicated drug classifications for the historical drug claims of the particular set of historical drug claims, the third-party-indicated drug classifications including a generic drug classification, a brand drug classification, and a specialty drug classification;

classifying each historical drug claim of the particular set of historical drug claims into one or more third-party-indicated drug classifications of the third-party-indicated drug classifications based on the data indicators, the classifying disregarding the corresponding PBM-indicated drug classification;

obtaining, from the one or more third-party systems, price inflation parameters and utilization inflation parameters for each third-party-indicated drug classification of the one or more third-party-indicated drug classifications, the third party systems being different than the remote database, the particular remote client system and the plurality of PBM systems;

obtaining historical utilization data associated with the particular set of historical drug claims;

using the particular set of historical drug claims from the remote database to project costs forward by applying the price inflation parameters to the pricing information of each bid of said one or more bids based on the one or more drug third-party-indicated classifications, and applying the utilization inflation parameters to the historical utilization data associated with the particular set of historical drug claims;

calculating a corresponding estimated plan cost for each bid of the one or more bids based on the projecting costs forward, the corresponding estimated plan cost of each bid of the one or more bids having accounted for price inflation and utilization inflation based on the same price inflation parameters, the same utilization inflation parameters, and the same third-party-indicated drug classifications;

calculating a contract terms cost for the contract terms of each bid of the one or more bids;

generating scores for each bid of said one or more bids based on the corresponding estimated plan cost and on the contract terms cost; and sending at least one bid of the one or more bids and at least one score of the scores to said particular remote client system to support selection of the drug prescription plan.

13. The computer-implemented method of claim 1, further comprising:

receiving one or more bid scenarios from a particular remote PBM system of the one or more of said plurality of remote PBM systems, each of said one or more bid scenarios including particular pricing information and particular contract terms being considered as a particular bid to be submitted; and providing one or more particular estimated plan cost responses to the particular remote PBM system as feedback to the received one or more bid scenarios.

14. The computer-implemented method of claim 1, wherein the particular entity initiated the RFP process.

15. The computer-implemented method of claim 1, wherein the particular entity is not associated with an associated entity that initiated the RFP process.

* * * * *